US00PP35117P2

(12) United States Plant Patent
Holtmaat

(10) Patent No.: US PP35,117 P2
(45) Date of Patent: Apr. 18, 2023

(54) ***HEUCHERA* PLANT NAMED 'TONCKA 306'**

(50) Latin Name: ***Heuchera* hybrid**
Varietal Denomination: Toncka 306

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/961,662

(22) Filed: Oct. 7, 2022

(30) Foreign Application Priority Data

Nov. 11, 2021 (QZ) ..... PBR 20212915

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Karen M Redden
(74) *Attorney, Agent, or Firm* — Penny J Aguirre

(57) ABSTRACT

A new cultivar of *Heuchera* plant named 'Toncka 306' that is characterized by its glossy foliage that is green in color, and have a small black markings in the centers surrounding the main veins, its floriferous blooming habit, its remontant flowering, its small flowers that are white in color, and its sterile flowers.

2 Drawing Sheets

Botanical classification: *Heuchera* hybrid.
Cultivar designation: 'Toncka 306'.

CROSS REFERENCE TO A RELATED APPLICATION

This application claims priority to European Community Plant Variety Office (CPVO) Plant Breeder's Rights Application No. 2021/2915, filed Nov. 11, 2021. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'Toncka 306' and is hereinafter referred to by its cultivar name 'Toncka 306'.

The new cultivar was discovered as a chance seedling in a trial field by the Inventor in Zuidwolde, The Netherlands in July of 2019. The source of the seedling was from seed collected in 2019 from open pollinated plants in a trial field that contained numerous unnamed and unpatented proprietary *Heuchera* seedlings from the Inventor's breeding program. The parentage of 'Toncka 306' is therefore unknown.

Asexual propagation of the new cultivar was first accomplished under the direction of the Inventor by tissue culture initiated from meristem tissue in February of 2021 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Toncka 306' as a new and unique cultivar of *Heuchera*.

1. 'Toncka 306' exhibits glossy foliage that is green in color, and have a small black markings in the centers surrounding the main veins.
2. 'Toncka 306' exhibits a floriferous blooming habit.
3. 'Toncka 306' exhibits remontant flowering.
4. 'Toncka 306' exhibits small flowers that are white in color.
5. 'Toncka 306' exhibits sterile flowers.

'Toncka 306' can be most closely compared to the *Heuchera* cultivars 'High Hopes' (U.S. Plant Pat. No. 31,100) and 'Pretty Perrine' (U.S. Plant Pat. No. 26,112). 'High Hopes' is similar to 'Toncka 306' in plant size and flower color. 'High Hopes' differs from 'Toncka 306' in having foliage that is lighter yellow-green in color with a larger area of markings around the veins with a secondary color, and foliage that is less glossy. 'Pretty Perrine' is similar to 'Toncka 306' in flower color. 'Pretty Perrine' differs from 'Toncka 306' in having a shorter plant height, foliage with a larger area of markings around the veins with a secondary color, and inflorescences that are shorter in height.

BRIEF DESCRIPTION OF THE DRAWINGS

The accompanying color photographs illustrate the overall appearance and distinct characteristics of the new *Heuchera*. The photographs were taken of a plant 18 months in age of the new cultivar as grown outdoors in a 19-cm container in Zuidwolde, The Netherlands.

The photograph in FIG. 1 provides a side view of a plant of 'Toncka 306' in bloom.

Figure 1:
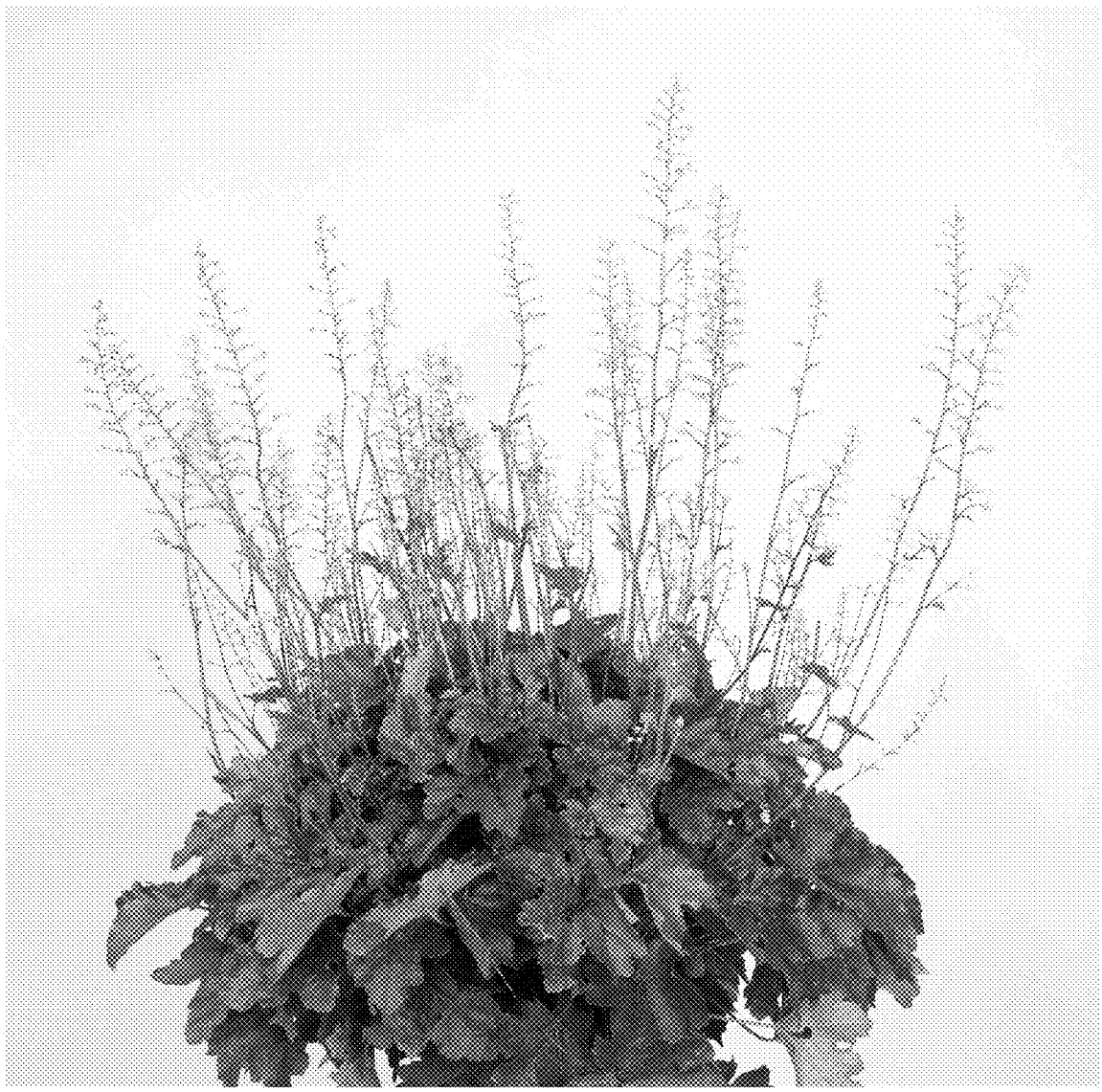
Figure 2:
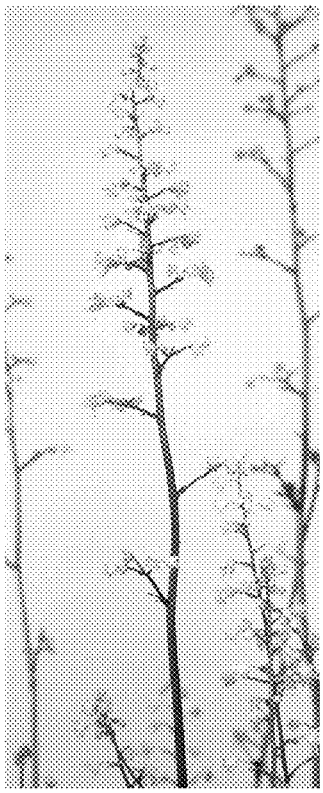

The photograph in FIG. 2 provides a close up of an inflorescence of 'Toncka 306'.

Figure 3:
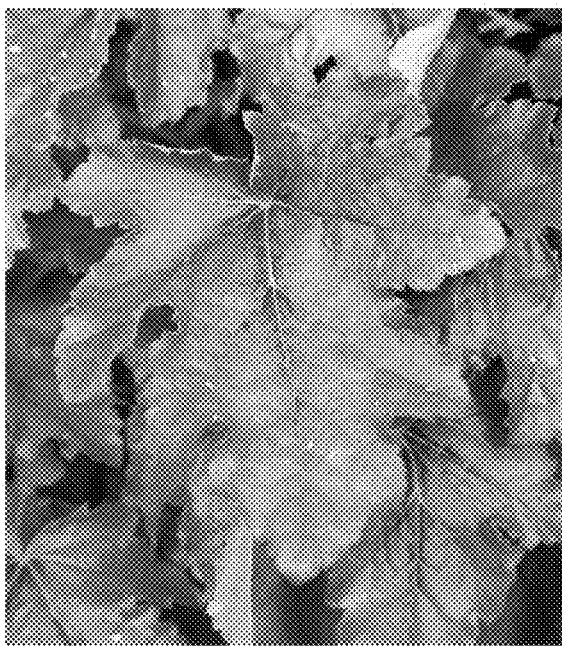

The photograph in FIG. 3 provides a close up view of a leaf of 'Toncka 306'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—12 weeks in midsummer to late summer and early fall in The Netherlands.

*Plant type.*—Herbaceous perennial.

*Plant habit.*—Globular with inflorescences held above the foliage.

*Height and spread.*—An average of 35 cm in height (soil level to top of foliar plane), average of 75 cm in height (soil level to top of floral plane) and 65 cm in spread as an 18 month-old plant.

*Cold hardiness.*—At least in U.S.D.A. Zone 3.

*Diseases and pests.*—No susceptibility or resistance to pests or diseases has been observed.

*Root description.*—Fibrous roots on woody rootstalks, 158D in color.

*Propagation.*—Tissue culture.

*Root development.*—An average of 3 weeks for root initiation and 6 weeks to produce a rooted cutting.

*Growth rate.*—Vigorous.

*Branching habit.*—Flowering stems emerge from basal rosette, an average of 35 rosettes per plant, no lateral branches.

Foliage description:

*Leaf shape.*—Broad ovate in outline, very slightly concave.

*Leaf division.*—Simple.

*Leaf base.*—Hastate, lobes free to touching.

*Leaf apex.*—Short and abruptly acute.

*Leaf venation.*—Laciniate, upper surface 144A and 144B, lower surface 145A.

*Leaf margins.*—Crenate with abruptly acute tips on each tooth, moderately coarsely undulate.

*Leaf attachment.*—Petiolate.

*Leaf arrangement.*—Alternate in basal rosettes.

*Leaf lobes.*—Lobed, an average of 7 to 9 lobes, medium in depth, divergent, lobe margins free to touching.

*Leaf surface.*—Upper surface; smooth and slightly velvety, non-rugose, slightly glossy, lower surface; smooth, non-rugose, very slightly glossy, both surfaces; pubescent, moderately covered with very short strigose hairs 0.75 mm in length, closest to NN155D in color.

*Leaf color.*—Young upper surface; 144A, area adjacent to main veins at base of lamina 200A and 200B, young lower surface; 143C, area adjacent to main veins at base of lamina N199A, mature upper surface; a blend of 137A and 146A, area adjacent to main veins at base and in center of lamina 203A, mature lower surface; a blend of 147B and 148B.

*Leaf size.*—An average of 12.9 cm in length and 11.7 cm in width.

*Leaf quantity.*—An average of 8 per basal rosette.

*Petioles.*—An average of 21.8 cm in length and 3 mm in diameter, medium strength, both surfaces slightly glossy, upper surface color 146C, tinged towards the base; 71B, lower surface color 144A, tinged towards the base; 177C, very densely covered with short, soft strigose hairs an average of 1.5 mm in length, 156D in color.

*Stipules.*—Leafy stipule at the base of each leaf, average 2.1 cm in length, average 6 mm in width, acute tip, 72A in color.

Flower description:

*Inflorescence type.*—Numerous small bell-shaped flowers arranged on panicles on peduncles emerging from a basal rosette.

*Inflorescence size.*—An average of 36.2 cm in height and 5.8 cm in diameter.

*Inflorescence number.*—An average of 50.

*Flower fragrance.*—None.

*Flower quantity.*—Average of 150 flowers per flowering stem, 6,500 per plant.

*Flower lastingness.*—Average of one week.

*Flower buds.*—Obovate to nearly orbicular in shape, an average of 3 mm in length and 2.75 mm in diameter, color; 150D, tip 150C, lower ⅓rd 151B, surface is matte and densely covered with very short glandular hairs an average of 0.2 mm in length and too small to measure color.

*Flower aspect.*—Slightly outward.

*Flower type.*—Single, campanulate.

*Flower size.*—Average of 9 mm in length and diameter.

*Petals.*—Average of 5, rotate arrangement and implanted in the hypanthium at base, oblanceolate in shape, margin is entire, apex is acute, base is long acuminate, upper and lower surface is glabrous, smooth and matte, an average of 4 mm in length and 1 mm in width, color when opening and fully open upper and lower surface; NN155D.

*Calyx.*—Campanulate, sepals fused to hypanthium, 3 mm in length, 4.5 mm in diameter.

*Sepals.*—An average of 5, lower 25% fused into campanulate hypanthium, ovate in shape, an average of 3 mm in length and 1.5 mm in width, margin is entire and fused into hypanthium, apex is obtuse, color; when opening and fully open upper surface NN155D, tip 145C, when opening and fully open lower surface N155D, tip 145B, both surfaces are matte and densely covered with very short glandular hairs an average of 0.2 mm in length and to small to measure color.

*Peduncle.*—An average of 65.9 cm in length and 3 mm in diameter, color; 144A, tinged 152A, primary flower aspect 65° to horizontal, secondary peduncle aspect to main peduncle 70°, moderate in strength, surface moderately glossy and densely covered with very short soft glandular hairs; average of 0.5 mm in length and to small to measure color.

*Pedicels.*—An average of 3 mm in length and 0.5 mm in diameter, 195B in color, primary flower aspect straight on top of secondary pedicel, secondary and tertiary flower aspect is 30°, moderate in strength, surface matte and densely covered with very short soft glandular hairs; average of 0.2 mm in length and too small to measure color.

Reproductive organs:

*Gynoecium*.—Pistils; 2, 2 mm in length, stigma; club-shaped, 0.2 mm in diameter, style; an average of 1.8 mm in length and NN155D in color, ovary; 157D in color.

*Androecium*.—Stamens; 5, anthers; ovate in shape, average of 0.3 mm in length and width, NN155D in color, filament; 2 mm in length and N155B in color, pollen; low in quantity, 164A in color.

*Seed/fruit*.—No fruit or seeds have been observed, flowers are sterile.

It is claimed:

1. A new and distinct cultivar of *Heuchera* plant named 'Toncka 306' as herein illustrated and described.

* * * * *